United States Patent [19]  
Takisawa et al.

[11] Patent Number: 4,958,033  
[45] Date of Patent: Sep. 18, 1990

[54] PROCESS FOR PREPARING ALCOHOLS

[75] Inventors: Yukihisa Takisawa; Nobuharu Kono; Kenji Saito; Hiroshi Yamachika, all of Osaka, Japan

[73] Assignee: Sumitomo Chemical Company, Limited, Osaka, Japan

[21] Appl. No.: 912,220

[22] Filed: Sep. 26, 1986

Related U.S. Application Data

[63] Continuation of Ser. No. 563,524, Dec. 20, 1983, abandoned.

[30] Foreign Application Priority Data

Dec. 24, 1982 [JP] Japan ................. 57-230585

[51] Int. Cl.$^5$ ................. C07C 29/00; C07D 281/00
[52] U.S. Cl. ................. 549/59; 549/60; 549/78; 549/472; 549/497; 568/807; 568/808; 568/809; 568/813; 568/816; 568/822; 568/838; 568/839; 568/878; 568/907
[58] Field of Search ............. 568/873, 874, 807, 808, 568/809, 813, 818, 822, 838, 839, 878, 907; 549/78, 59, 60, 472, 497

[56] References Cited

U.S. PATENT DOCUMENTS 4,087,468 5/1978 Solomon .

OTHER PUBLICATIONS

Wagner "Synthetic Organic Chemistry", (1985) pp. 160–167.
Sumitomo Chemical publication dated Jul. 27, 1981, EP-73569.

*Primary Examiner*—Alan Siegel
*Attorney, Agent, or Firm*—Birch, Stewart, Kolasch & Birch

[57] ABSTRACT

A process for preparing an alcohol of the formula:

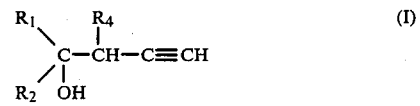

(I)

or

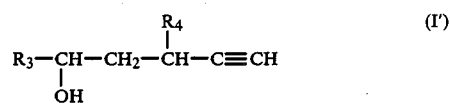

(I')

by reacting a carbonyl compound of the formula:

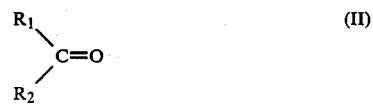

(II)

or an oxirane of the formula:

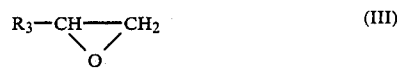

(III)

magnesium and a propargyl halide of the formula:

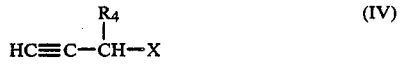

(IV)

followed by hydrolysis, characterized in that the carbonyl compound (II) or the oxirane compound (III) and the propargyl halide (IV) are reacted simultaneously with magnesium in an inert solvent in the presence of zinc or a halide thereof.

11 Claims, No Drawings

PROCESS FOR PREPARING ALCOHOLS

This application is a continuation of application Ser. No. 563,524, filed on Dec. 20, 1983, now abandoned.

This invention relates to a process for preparing alcohols. More particularly, it relates to a process for preparation of alcohols of the formula:

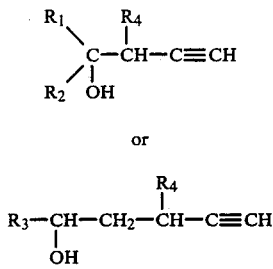

or $$R_3-CH-CH_2-\underset{\underset{OH}{|}}{CH}-C\equiv CH \quad (I')$$

wherein $R_1$ and $R_2$ are, the same or different, each a hydrogen atom, a straight, branched or cyclic alkyl, alkenyl or alkynyl group having not more than 14 carbon atoms, a phenyl group, a naphthyl group, a benzyl group, a furyl group or a thienyl group, provided that when either one of $R_1$ and $R_2$ represents a hydrogen atom, the other is not a hydrogen atom, $R_3$ is a hydrogen atom, a straight or branched alkyl group having not more than 6 carbon atoms or a phenyl group, and $R_4$ is a hydrogen atom or a methyl group.

The alcohols of the formula (I) or (I') are useful as intermediates for the synthesis of chemical substances such as agricultural chemicals, medicines and perfumes.

For the production of alcohols from carbonyl compounds or oxirane compounds, there is known a general method comprising the step of the so-called Grignard reaction, i.e. the reaction of a carbonyl compound or oxirane compound with a Grignard reagent as previously prepared. Typical examples of such methods are a procedure wherein 3-bromo-1-butyne and magnesium are reacted in ether in the presence of mercuric chloride as a catalyst to provide the Grignard reagent, and then this Grignard reagent is reacted with a carbonyl compound (J. Org. Chem., Vol. 42, No. 11, 1960 (1977)), and a procedure wherein propargyl bromide and magnesium are reacted in ether in the presence of mercuric chloride as a catalyst to provide the Grignard reagent, and then this Grignard reagent is reacted with 5-methylfurfural in tetrahydrofuran (U.S. Pat. No. 3,892,782). As seen in these conventional procedures, it has been considered advantageous to use a mercury compound as the catalyst in connection with the preparation of a Grignard reagent. In those procedures, however, the recovery of the mercury compound used as the catalyst is important and essential in order to avoid any pollution problem. Further, the use of large amounts of magnesium and of propargyl halide is necessary in order to attain a considerable yield of the Grignard reagent unless special and expensive apparatus is employed. These factors are extremely disadvantageous for industrial adoption of such processes.

Besides, there is known a process for preparing alcohols in one step, i.e. by simultaneous reaction of a carbonyl compound and a propargyl halide (Japanese Patent Publn. (unexamined) No. 130618/1978; U. Org. Chem., 44, No. 9, 1438 (1979)). This process requires the use of a mercuric compound as a catalyst and is thus industrially disadvantageous.

In order to provide an industrially advantageous process for preparation of the alcohols (I) or (I') according to the Grignard reaction without using any mercury compound as the catalyst and without employing any special and expensive apparatus, an extensive study has been made. As the result, it has now been found that the presence of zinc or its halide in the reaction of magnesium with the carbonyl compound or the oxirane compound and a propargyl halide and also the simultaneous reaction of the carbonyl compound or the oxirane compound and a propargyl halide with magnesium provides such a process. This invention is based on the above finding.

According to this invention, there is provided a process for preparation of the alcohol (I) or (I') by reacting a carbonyl compound of the formula:

wherein $R_1$ and $R_2$ are each as defined above, or an oxirane of the formula:

wherein $R_3$ is as defined above, magnesium and a propargyl halide of the formula:

wherein X is a halogen atom (e.g. chlorine, bromine), followed by hydrolysis, characterized in that the carbonyl compound (II) or the oxirane compound (III) and the propargyl halide (IV) are reacted simultaneously with magnesium in an inert solvent in the presence of zinc or its halide.

Examples of the carbonyl compound (II) include aldehydes (e.g. acetaldehyde, propionaldehyde, n-valeraldehyde, isobutylaldehyde, cyclohexylaldehyde, crotonaldehyde, 2-cyclopentenylaldehyde, 2-heptenal, 2-propynal, benzaldehyde, phenylacetaldehyde, furfural, 5-methylfurfural, 5-ethylfurfural, naphthylaldehyde, 2-thiophenaldehyde) and ketones (e.g. acetone, methyl ethyl ketone, methyl isobutyl ketone, cyclopentanone, cyclohexanone, 4,6-dimethyloctan-2-one, methyl vinyl ketone, 3-hexyn-2-one, acetophenone, benzophenone). Examples of the oxirane compound (III) are ethylene oxide, propylene oxide, butylene oxide, styrene oxide, etc. As the propargyl halide (IV), there may be exemplified propargyl chloride, propargyl bromide, 3-chloro-1-butyne, 3-bromo-1-butyne, etc. Their mixtures are also usable.

In the process of the invention, it is an essential feature to use zinc or its halide as an activator in place of a mercuric compound. Examples of the zinc halide are zinc chloride, zinc bromide, zinc iodide, etc. These may be used alone or in combination. Zinc or its halide is usually employed in an amount of 0.05 to 0.5 mole to one mole of the starting carbonyl compound (II) or the oxirane compound (III). The entire amount of zinc or its halide may be present in the reaction system from the start of the reaction. Alternatively, its portion may be introduced into the reaction system together with the carbonyl compound (II) or the oxirane compound (III) and/or the propargyl halide (IV).

As the inert solvent, the use of tetrahydrofuran is the most preferred. Its amount may be usually not less than 2 parts by weight to one part by weight of the carbonyl compound (I) or the oxirane compound (III). Although there is no upper limit to the amount of tetrahydrofuran, it is appropriate that the maximum amount be decided depending upon the reaction scale. Any other inert solvent may be also employed alone or in combination with tetrahydrofuran so as to make the recovery or re-use of the solvent easy. As the other solvent, there are exemplified aromatic hydrocarbons (e.g. benzene, toluene, xylene), ethers (e.g. tetrahydropyran, furan, ether), etc.

It is another essential feature of the invention to react the carbonyl compound (II) or the oxirane compound (III) and the propargyl halide (IV) simultaneously onto magnesium. For instance, the carbonyl compound (II) or the oxirane compound (III) and the propargyl halide (IV) may be separately and in parallel added to magnesium dissolved in the inert solvent. Further, for instance, a mixture of the carbonyl compound (II) or the oxirane compound (III) and the propargyl halide (IV) may be continuously or intermittently added to magnesium dissolved in the inert solvent. In either of these types of addition, any of the carbonyl compound (II) or the oxirane compound (III) and the propargyl halide (IV) may previously be dissolved in the inert solvent.

The simultaneous reaction as above noted is quite advantageous from an industrial point of view, because the Grignard reaction product is obtainable in a good yield at a higher temperature even when magnesium and the propargyl halide are used in slightly excessive amounts, whereby the cost of the starting materials and the energy for elimination of the heat generated in the reaction system are much decreased.

The term "simultaneous" or "simultaneously" used herein in conjunction with the introduction of the respective components, i.e. the carbonyl compound (II) or the oxirane compound (III) and the propargyl halide (IV), into the reaction system does not necessarily mean their addition to the reaction system always simultaneously. For instance, the sole continuous or intermittent addition of either one of those components to the reaction system should be understood to be still substantially within the framework of the term "simultaneous" or "simultaneously" provided that said addition is made within a reasonably short time after or before the addition of the other component.

The reaction temperature is favored to be within a range of 10° to 60° C., because too low of a temperature leads to a lowering of the reaction efficiency, while too high of a temperature results in an excessive reactivity. There is no particular limitation on the reaction pressure. When the reaction is conducted under a reduced pressure, it is considered to be easier to eliminate the excessive heat by refluxing and to control the reaction temperature therewith.

The amount of the propargyl halide (IV) in the reaction is generally from 1.05 to 1.5 moles, preferably from 1.1 to 1.3 moles to 1 mole of the carbonyl compound (II) or the oxirane compound (III). The amount of magnesium is preferably not less than 1.05 moles, although there is no particular limitation on its upper range.

In connection with the practice of the Grignard reaction according to the invention, it is advantageous that magnesium is treated with a slight amount of the propargyl halide (IV) in the presence of metal zinc or a zinc halide prior to the simultaneous reaction of the carbonyl compound (II) or the oxirane compound (III) and the propargyl halide (IV) with the magnesium.

The thus prepared Grignard reaction product is then subjected to hydrolysis to obtain the alcohol (I) or (I'). The hydrolysis may be carried out in a conventional manner. Thus, it may be effected by treatment with ammonium chloride, a mineral acid (e.g. hydrochloric acid, sulfuric acid) or an organic acid (e.g. acetic acid) in an aqueous medium. The resultant hydrolyzed product is purified, if necessary, by any conventional procedure such as distillation or extraction to give the objective alcohol (I) or (I') with an excellent yield and a high purity.

Practical and presently preferred embodiments of the invention are illustratively shown in the following Examples, wherein % is by weight unless otherwise indicated.

EXAMPLE 1

In a 500 ml volume round bottom flask dried and flushed with nitrogen, there were charged granular magnesium (18.2 g), dry zinc chloride (13.6 g) and dry tetrahydrofuran (110 g). Propargyl bromide (0.88 g) was added thereto at 10° C while stirring. The resultant mixture was kept in an adiabatic condition, whereupon the reaction proceeded. When the heat generation stopped, a mixture of 5-methylfurfural (55.06 g), propargyl bromide (61.6 g) and xylene (100 g) was dropwise added to the reaction mixture at 40° C in 1.5 hours while stirring under cooling. The resultant mixture was kept at room temperature for 30 minutes while stirring. After completion of the reaction, the thus obtained mixture and an aqueous solution (225 g) of 1.82 % acetic acid and 13.6 % sulfuric acid were simultaneiously poured into water (250 g) at a temperature of not lower than 30° C and at a pH of not less than 4 in 20 minutes while stirring and then kept at room temperature for 30 minutes under stirring. Upon termination of the reaction, the mixture was separated, and an aqueous layer was removed. The oily layer was washed with the aqueous solution of 5 % sodium carbonate. The solvent was removed, and the residue was distilled under reduced pressure (73°–75° C./0.75 mmHg) to give 2-(1-hydroxy3-butynyl)-5-methylfuran (63.1 g) in a yield of 84 % (based on the starting 5-methylfurfural).

EXAMPLE 2

In the same flask as in Example 1, there were charged granular magnesium (18.2 g), dry zinc chloride (10.2 g) and dry tetrahydrofuran (110 g). Propargyl bromide (0.88 g) was added thereto at 10° C while stirring. The resultant mixture was kept in an adiabatic condition, whereupon the reaction proceeded. When the heat generation stopped, a mixture of furfural (48.0 g), propargyl bromide (73.5 g) and toluene (110 g) was dropwise added to the reaction mixture at 30° C in 3 hours while stirring under cooling. The resultant mixture was kept at room temperature for 30 minutes while stirring. After completion of the reaction, the reaction mixture was treated in the same manner as in Example 1 and distilled under reduced pressure (65°–66° C./ 0.45 mmHg) to give 2-(1-hydroxy-3-butynyl)-furan (61.3 g) in a yield of 90% (based on the starting furfural).

EXAMPLE 3

In the same flask as in Example 1, there were charged granular magnesium (14.6 g), dry zinc chloride (6.8 g) and dry tetrahydrofuran (110 g). Propargyl bromide (0.88 g) was added thereto at 10° C. while stirring. The resultant mixture was kept in an adiabatic condition, whereupon the reaction proceeded. When the heat generation stopped, a mixture of 5-methylfurfural (55.06 g), propargyl bromide (64.5 g), tetrahydrofuran (55 g) and isopropyl ether (55 g) was dropwise added to the reaction mixture at 50° C. in 1.5 hours while stirring under cooling. The resultant mixture was kept at room temperature for 30 minutes while stirring. After completion of the reaction, the reaction mixture was treated in the same manner as in Example 1 to give 2-(1-hydroxy-3-butynyl)-5-methylfuran (60.5 g) in a yield of 81% (based on the starting 5-methylfurfural).

EXAMPLE 4

In the same flask as in Example 1, there were charged granular magnesium (24.3 g), dry zinc bromide (16.9 g) and dry tetrahydrofuran (110 g). Propargyl chloride (0.55 g) was added thereto at 10° C. while stirring. The resultant mixture was kept in an adiabatic condition, whereupon the reaction proceeded. When the heat generation stopped, a mixture of 5-methylfurfural (55.06 g), propargyl chloride (47.9 g) and tetrahydrofuran (110 g) was dropwise added to the reaction mixture at 35° C. in 2 hours while stirring under cooling. The resultant mixture was kept at room temperature for 30 minutes while stirring. After completion of the reaction, the reaction mixture was treated in the same manner as in Example 1 to give 2-(1-hydroxy-3-butynyl)-5-methylfuran (60.3 g) in a yield of 81% (based on the starting 5-methylfurfural).

EXAMPLE 5

In the same flask as in Example 1, there were charged granular magnesium (18.2 g), dry zinc chloride (20.4 g) and dry tetrahydrofuran (220 g). Propargyl chloride (0.55 g) was added thereto at 10° C. while stirring. The resultant mixture was kept in an adiabatic condition, whereupon the reaction proceeded. When the heat generation stopped, a mixture of 5-methylfurfural (55.06 g), propargyl chloride (38.6 g), propargyl bromide (11.9 g) and toluene (55 g) was dropwise added to the reaction mixture at 30° C. in 6 hours while stirring under cooling. The resultant mixture was kept at room temperature for 30 minutes while stirring. After completion of the reaction, the reaction mixture was treated in the same manner as in Example 1 to give 2-(1-hydroxy-3-butynyl)-5-methylfuran (64.4 g) in a yield of 86% (based on the starting 5-methylfurfural).

EXAMPLE 6

In the same flask as in Example 1, there were charged granular magnesium (18.2 g), dry zinc chloride (10.2 g) and dry tetrahydrofuran (100 g). 3-Chloro-1-butyne (0.66 g) was added thereto at 10° C. while stirring. The resultant mixture was kept in an adiabatic condition, whereupon the reaction proceeded. When the best generation stopped, a mixture of furfural (48 g), 3-chloro-1-butyne (45.88 g) and toluene (125 g) was dropwise added to the reaction mixture at 45° C. in 1.5 hours while stirring under cooling. The resultant mixture was kept at room temperature for 30 minutes while stirring. After completion of the reaction, the reaction mixture was treated in the same manner as in Example 1 and distilled under reduced pressure (66°–68° C./1 mmHg) to give 2-(1-hydroxy-2-methyl-3-butynyl)-furan (63.8 g) in a yield of 84% (based on the starting furfural).

EXAMPLE 7 to 15

In the same manner as in Example 1 but under the conditions as specified in Table 1, there were produced the alcohols (I) or (I') shown in Table 1.

TABLE 1

| Example No. | Starting materials | | | | Reaction temperature and adding time | Alcohols (I) or (I') | |
|---|---|---|---|---|---|---|---|
| | Mg (g) | Carbonyl compound (II) or oxirane compound (III) | Propargyl halide | Zinc or its halide | Solvent | | |
| | | | | | | Structure | Amount (Yield) | B.P. |
| 7 | 18.2 | PhCHO (53.1 g) | CH≡CCH₂Br (74.3 g) | ZnBr₂ (16.9 g) | THF (100 g) Furan (125 g) | 30° C.; 2 hrs | Ph-CH(OH)CH₂C≡CH | 61.2 g (92%) | 75–77° C./ 0.4 mm Hg |
| 8 | 21.9 | CH₃(CH₂)₃CHO (43.1 g) | CH≡CCH₂Br (74.3 g) | ZnCl₂ (12.3 g) | THF (240 g) | 35° C.; 1.5 hrs | CH₃(CH₂)₃CH(OH)CH₂C≡CH | 49.7 g (78%) | 62–64° C./ 10 mm Hg |
| 9 | 18.2 | (CH₃)₂CHCH₂COCH₃ (50.1 g) | CH≡CCH₂Br (74.3 g) | ZnCl₂ (10.2 g) | THF (300 g) | 35° C.; 2 hrs | (CH₃)₂CHCH₂C(CH₃)(OH)CH₂C≡CH | 60.3 g (86%) | 55–57° C./ 10 mm Hg |
| 10 | 18.2 | cyclopentanone (42.1 g) | CH≡CCH₂Br (74.3 g) | ZnCl₂ (10.2 g) | THF (100 g) Toluene (125 g) | 30° C.; 2 hrs | 1-(2-propynyl)cyclopentanol | 52.2 g (84%) | 60–62° C./ 9 mm Hg |
| 11 | 18.2 | H₂C=CHCOCH₃ (35.1 g) | CH≡CCH₂Br (74.3 g) | ZnCl₂ (10.2 g) | THF (225 g) | 55° C.; 1 hr | H₂C=CHC(CH₃)(OH)CH₂C≡CH | 39.8 g (70%) | 43–46° C./ 15 mm Hg |
| 12 | 22.1 | CH₃(CH₂)₃CH=CHCHO (56.1 g) | CH≡CCH₂Br (77.3 g) | ZnCl₂ (12.2 g) | THF (245 g) | 35° C.; 1.5 hrs | CH₃(CH₂)₃CH=CHCH(OH)CH₂C≡CH | 60.6 g (78%) | 65–69° C./ 4 mm Hg |
| 13 | 18.2 | CH₃CH—CH₂ (oxirane) (29.0 g) | CH≡CCH₂Br (74.3 g) | ZnCl₂ (10.2 g) | THF (225 g) | 40° C.; 0.5 hr | CH₃CH(OH)CH₂CH₂C≡CH | 36.1 g (70%) | 55–58° C./ 15 mm Hg |

TABLE 1-continued

| Example No. | Starting materials | | | | Zinc or its halide | Solvent | Reaction temperature and adding time | Alcohols (I) or (I') | | |
|---|---|---|---|---|---|---|---|---|---|---|
| | Mg (g) | Carbonyl compound (II) or oxirane compound (III) | Propargyl halide | | | | | Structure | Amount (Yield) | B.P. |
| 14 | 36.5 | ⟨S⟩—CHO (56.1 g) | CH≡CCH(CH₃)Br (83.1 g) | | Zn (9.8 g) | THF (300 g) | 35° C.; 2 hrs | ⟨S⟩—CH(OH)CH(CH₃)C≡CH | 63.9 g (84%) | 76–80° C./ 0.9 mm Hg |
| 15 | 18.2 | ⟨S⟩—CHO (56.1 g) | CH≡CCH₂Br (11.0 g) CH≡CCH₂Cl (38.6 g) | | ZnCl₂ (10.2 g) | THF (175 g) Isopropyl ether (50 g) | 30° C.; 3 hrs | ⟨S⟩—CH(OH)CH₂C≡CH | 67.7 g (89%) | 74–78° C./ 0.6 mm Hg |

What is claimed is:

1. A process for preparing an alcohol of the formula:

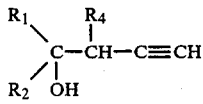 (I)

or

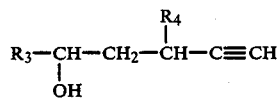 (I')

wherein $R_1$ and $R_2$ are, the same or different, each a hydrogen atom, a straight, branched or cyclic alkyl, alkenyl or alkynyl group having not more than 14 carbon atoms, a phenyl group, a naphthyl group, a benzyl group, a furyl group or a thienyl group, provided that when either one of $R_1$ and $R_2$ represents a hydrogen atom, the other is not a hydrogen atom, $R_3$ is a hydrogen atom, a straight or branched alkyl group having not more than 6 carbon atoms or a phenyl group and $R_4$ is a hydrogen atom or a methyl group, by reacting a carbonyl compound of the formula:

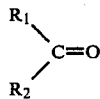 (II)

wherein $R_1$ and $R_2$ are each as defined above, or an oxirane of the formula:

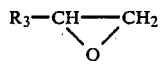 (III)

wherein $R_3$ is as defined above, magnesium and a propargyl halide of the formula:

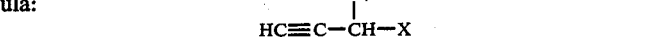 (IV)

wherein X is a halogen atom and $R_4$ is as defined above, followed by hydrolysis, wherein the carboxyl compound (II) or the oxirane compound (III) and the propargyl halide (IV) are simultaneously charged into a reaction system of magnesium in an inert solvent in the presence of zinc or a halide thereof.

2. The process according to claim 1, wherein the inert solvent is tetrahydrofuran.

3. The process according to claim 1, wherein the zinc halide is selected from the group consisting of zinc chloride, zinc bromide and zinc iodide.

4. The process according to claim 1, wherein zinc or a halide thereof is used in an amount of from 0.05 to 0.5 mole per one mole of the carbonyl compound or the oxirane compound.

5. The process according to claim 1, wherein X in the propargyl halide is a chlorine atom or a bromine atom.

6. The process according to claim 1, wherein the carbonyl compound II is an aldehyde selected from the group consisting of acetaldehyde, propionaldehyde, n-valeraldeyde, isobutylaldehyde, cyclohexylaldehyde, crotonaldehyde, 2-cyclopentenylaldehyde, 2-heptenal, 2-propynal, benzaldehyde, phenylacetaldehyde, furfural, 5-methylfurfural, 5-ethylfurfural, naphthylaldehyde and 2-thiophenaldehyde.

7. The process according to claim 1, wherein the carbonyl compound II is a ketone selected from the group consisting of acetone, methyl ethyl ketone, methyl isobutyl ketone, cyclopentanone, cyclohexanone, 4,6-dimethyloctan-2-one, methyl vinyl ketone, 3-hexyn-2-one, acetophenone and benzophenone.

8. The process according to claim 1, wherein the oxirane compound (III) is a member selected from the group consisting of ethylene oxide, propylene oxide, butylene oxide and styrene oxide.

9. The process according to claim 1, wherein the propargyl halide (IV) is a member selected from the group consisting of propargyl chloride, propargyl bromide, 3-chloro-1-butyne and 3-bromo-1-butyne.

10. The process according to claim 6, wherein the aldehyde is furfural.

11. The process according to claim 6, wherein the aldehyde is 5-methylfurfural.

* * * * *